United States Patent [19]

Tilles

[11] 4,094,895
[45] June 13, 1978

[54] PROCESS FOR PREPARATION OF O-(SUBSTITUTED)BENZYL THIOCARBAMATES

[75] Inventor: Harry Tilles, El Cerrito, Calif.

[73] Assignee: Stauffer Chemical Company, Westport, Conn.

[21] Appl. No.: 828,456

[22] Filed: Aug. 29, 1977

Related U.S. Application Data

[62] Division of Ser. No. 710,505, Aug. 2, 1976.

[51] Int. Cl.² .......................................... C07C 153/09
[52] U.S. Cl. ............................................... 260/455 A
[58] Field of Search .................................. 260/455 A

[56] References Cited

U.S. PATENT DOCUMENTS 3,907,854  9/1975  Bolth et al. ..................... 260/455 A Primary Examiner—Lewis Gotts
Assistant Examiner—Robert C. Whittenbaugh
Attorney, Agent, or Firm—Joel G. Ackerman

[57] ABSTRACT

Novel compounds having the formula

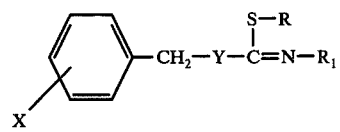

in which X is hydrogen, mono- or dihalo or 2-methyl; Y is oxygen or sulfur; R is alkyl, lower alkenyl, chloro-lower alkenyl, carbomethoxymethyl or methyl-thiomethyl; and $R_1$ is lower alkyl, lower alkenyl or p-chlorobenzyl, provided that if X is 4-chloro, R is other than methyl-thiomethyl. The novel compounds of this type possess aphicidal activity.

Also disclosed is a novel process for making O-(substituted)benzyl thiocarbamate intermediates for these compounds.

2 Claims, No Drawings

PROCESS FOR PREPARATION OF O-(SUBSTITUTED)BENZYL THIOCARBAMATES

This is a division, of application Ser. No. 710,505, filed Aug. 2, 1976, pending.

DESCRIPTION OF THE INVENTION

This invention relates to novel S-alkyl carbonimidothioates and dithioates. More particularly, this invention relates to novel compounds having the formula

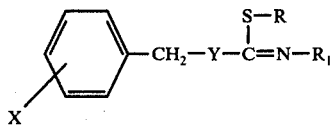

in which X is hydrogen, mono- or dihalo or 2-methyl; Y is oxygen or sulfur; R is alkyl, lower alkenyl, chloro-lower alkenyl, carbomethoxymethyl or methyl-thiomethyl; and $R_1$ is lower alkyl, lower alkenyl or p-chlorobenzyl, provided that if X is 4-chloro, R is other than methyl-thiomethyl.

Preferred embodiments with respect to X are monohalo, especially 2- and 3-halo, and dichloro, more particularly 2-fluoro, 2-chloro, 2-bromo, 2-iodo, 3-chloro, 2,5-dichloro and 3,4-dichloro. In a particularly preferred embodiment, X is 2-chloro, R is alkyl or alkenyl and $R_1$ is lower alkyl.

By the term "alkyl" is meant to include such groups having either straight chain or branched chain configuration. For example, the alkyl group may be methyl, ethyl, n-propyl, isopropyl, n-butyl, sec.-butyl, isobutyl, tert.-butyl, n-pentyl, isopentyl, neopentyl, n-hexyl, neohexyl, n-heptyl, n-octyl, nonyl, decyl, dodecyl and the like. In a preferred embodiment, the term "alkyl" includes such groups having from 1 to 15 carbon atoms.

The terms "lower alkyl" and "chloro-lower alkyl" are meant to include such groups having from 1 to 6, preferably from 1 to 4, carbon atoms. For example, the lower alkyl group includes methyl, ethyl, n-propyl isopropyl, n-butyl, sec.-butyl, isobutyl, tert.-butyl and the like and chloro-lower alkyl groups may be various mono- or poly-substituted groups such as chloroethyl, chloropropyl groups and the like.

By the term "lower alkenyl" and "chloro-lower alkenyl" are meant to include such groups having from 2 to 6, preferably from 2 to 4 carbon atoms, in both straight and branched chain configurations. For example, the lower alkenyl group may be vinyl, allyl, 2-methylallyl, propenyl, 1-butenyl, 2-butenyl, isobutenyl, crotyl and the like and the chloro-lower alkenyl group may be such a group having from 2 to 4 carbon atoms, for instance, 2-chloroallyl.

In one embodiment Y is oxygen; the compounds are thioates. In another embodiment Y is sulfur; the compounds are dithioates.

In another aspect the invention relates to a method for controlling aphids by applying to the aphid or the habitat thereof an aphicidally effective amount of a compound having the formula

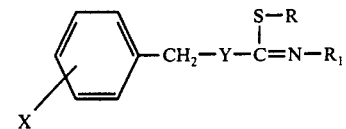

in which X, Y, R and $R_1$ are as defined above. Various methods of controlling aphids involve the use of the various embodiments of the compounds of the present invention mentioned herein.

In general, the compounds of the present invention can be prepared by conversion of an S- or O-benzylthiocarbamate to its sodium salt by treating it with an excess of sodium hydride in tetrahydrofuran. The sodium salt is then reacted with an alkyl halide, preferably an iodide, to yield the final product:

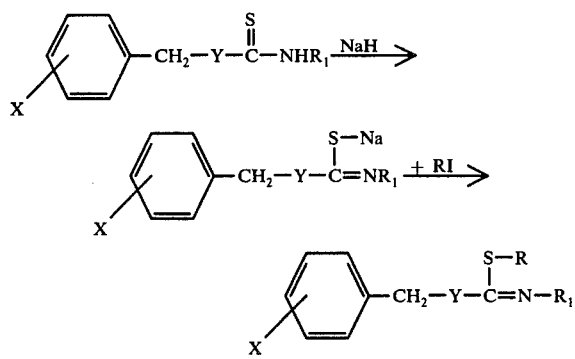

The following Examples 1–4 demonstrate the preparation of these compounds.

EXAMPLE 1

N-Methyl, O-2-chlorobenzyl, S-methallylcarbonimidothioate (Compound 35 herein).

To a 5 l. four-necked flask which contained an argon atmosphere was added 72.0 g. (3.00 moles) of granular sodium hydride and 1500 ml. of dry tetrahydrofuran. A solution of 539 g. (2.50 moles) of O-2-chlorobenzyl methylthiocarbamate dissolved in 400 cc. of dry tetrahydrofuran was then added dropwise with ice cooling over an interval of 14 minutes and a temperature range of 10°–18° C. The cooling bath was then removed and the mixture was allowed to stir for an additional 1¼ hours at 18°–23° C. Then 340 g. (3.75 moles) of 3-chloro-2-methylpropene which had recently been distilled was added over 6 minutes. The temperature rose from 23° to 35° C during the addition. After the addition an exothermic reaction continued for another hour and the temperature was maintained at about 40° C with appropriate cooling. When the exothermic reaction was over, the temperature was kept at about 40° C for 2½ more hours by applying heat. The reaction mixture was then cooled to 12° C under a strong argon purge and 300 ml. of ice water was carefully added to decompose the excess sodium hydride.

The mixture was then poured into 2500 ml. of water. The product separated as an oil which was phase separated and was washed with three portions of 500 ml. saturated salt solution. The oil was dried over anhydrous magnesium sulfate, filtered and the cake was washed with 3 small portions of ethyl ether. The combined filtrate was concentrated and evaporated. There was obtained 657 g. (97.4% of theory) of N-methyl, O-2-chlorobenzyl, S-methallylcarbonimidothioate. Gas chromatography showed this product to have a purity of 92.3 area %. The structure was confirmed by NMR (nuclear magnetic resonance) and IR (infra-red) analyses.

EXAMPLE 2

N-Methyl, O-2-chlorobenzyl, S-n-butylcarbonimidothioate (Compound 9 herein).

To a 5 l. four-necked flask which contained an argon atmosphere was added 72.0 g. (3.00 moles) of granular sodium hydride and 1500 ml. of dry tetrahydrofuran. A solution of 539 g. (2.50 moles) of O-2-chlorobenzyl methylthiocarbamate dissolved in 400 ml. of dry tetrahydrofuran was then added dropwise with ice cooling over an interval of 15 minutes and a temperature range of 8°–17° C. The cooling bath was then removed and the mixture was allowed to stir for an additional hour at 17°–22° C. Then 574 g. (3.12 moles) of 1-iodobutane was added dropwise over 10 minutes. The temperature was kept between 22°–30° C with ice cooling. The cooling bath was then removed and the mixture was stirred an additional 1¼ hour at 25°–27° C. It was then cooled in ice to 8° C under a strong argon purge and 300 ml. of ice water was carefully added to decompose the excess sodium hydride. When no more hydrogen was evolved, the mixture was poured into 2500 ml. of water and the oily product which separated was extracted with 500 ml. of ethyl ether. The ether solution was washed with three portions of 500 ml. saturated salt solution, dried over anhydrous magnesium sulfate, filtered and the filtrate was concentrated and evaporated. There was obtained 657 g. (96.7% of theory) of N-methyl, O-2-chlorobenzyl, S-butylcarbonimidothioate. Gas chromatography showed this product to have a purity of 93.5 area %. The structure was confirmed by NMR and IR analyses.

EXAMPLE 3

N-Ethyl, O-2-chlorobenzyl, S-n-propylcarbonimidothioate (Compound 31 herein).

To a 5 l. four-necked flask which contained an argon atmosphere was added 72.0 g. (3.00 moles) of granular sodium hydride and 1900 cc. of dry tetrahydrofuran. Then 574.3 g. (2.50 moles) of O-2-chlorobenzyl ethylthiocarbamate was added dropwise with ice cooling over an interval of 12 minutes at a temperature range of 9°–24° C. The mixture was stirred for 10 minutes and then 510 g. (3.00 moles) of 1-iodopropane was added dropwise over 6 minutes at 26°–40° C with ice cooling. The cooling bath was removed and the mixture was allowed to stir at 34°–27° C for 2¼ hours. It was then cooled in ice to 6° C under strong argon purge and 300 ml. of ice water was carefully added to decompose the excess sodium hydride. When no more hydrogen was evolved, the mixture was poured into 2500 ml. of water and the oily product which separated was extracted with 500 ml. of ethyl ether. The ether solution was washed with two 500 ml. portions of saturated salt solution, dried over anhydrous magnesium sulfate, filtered and the filtrate was concentrated and evaporated. There was obtained 660 g. (97.1% of theory) of N-ethyl, O-2-chlorobenzyl, S-propylcarbonimidothioate. Gas chromatography showed a purity of 89.4 area %. The structure was confirmed by NMR and IR analyses.

EXAMPLE 4

N-Methyl, S-n-propyl, S-2-chlorobenzylcarbonimidodithioate (Compound 115 herein).

To a 100 cc. three-necked flask under argon was added 0.72 g. (0.030 moles) of granular sodium hydride, 25 ml. of dry tetrahydrofuran and 10.20 g. (0.060 moles) of 1-iodopropane. The mixture was cooled to 3° C in an ice bath and then a solution of 4.64 g. (0.020 mole) of S-2-chlorobenzyl methyldithiocarbamate in 5 ml. of dry tetrahydrofuran was added over 6 minutes at 3°–8° C. The mixture was stirred for another hour at 3.5° C and then a few ml. of ethanol was added to decompose the excess sodium hydride. The mixture was poured into 200 ml. of water and the oil which separated was extracted with 150 ml. of ethyl ether. The ether solution was washed with two 50 ml. portions of water, dried over anhydrous magnesium sulfate, filtered, concentrated, and evaporated. There was obtained 5.0 g. (90.9% of theory) of N-methyl, S-propyl, S-2-chlorobenzylcarbonimidothioate. Gas chromatography showed a purity of 90.0 area %. The structure was confirmed by NMR and IR analyses.

The O-benzylthiocarbamates used as the starting materials in Examples 1–3, and analogous compounds for use in preparing the other monothioates disclosed herein, may be prepared by the reaction of an aromatic isothiocyanate with the appropriate benzyl alcohol using potassium tert.-butoxide and methyl sulfoxide, as described by Bauman, *J. Chem. & Eng. Data*, 11, 274 (1966). However, it has now been found that these O-(substituted) benzylthiocarbamates, which have the formula

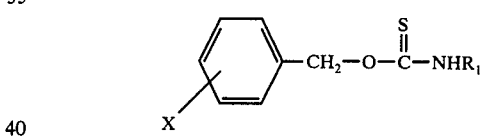

in which X and $R_1$ are as previously defined, can be advantageously prepared by a novel process in which the starting benzyl alcohol is first reacted with sodium hydride in tetrahydrofuran and the product reacted with the appropriate isothiocyanate. Example 5 demonstrates this process in the production of O-(2-chlorobenzyl)methylthiocarbamate.

EXAMPLE 5

To a 3 l. four-necked flask under argon was added 26.4 g. (1.10 mole) of granular sodium hydride and 500 ml. of dry tetrahydrofuran. A solution of 142.6 g. (1.00 mole) of 2-chlorobenzyl alcohol dissolved in 250 ml. of dry tetrahydrofuran was then added dropwise over an interval of 42 minutes without any cooling. The temperature rose from 23° to 36° C. The mixture was then heated to reflux (66° C) and held at reflux for 2 hours. It was then cooled to 4° C and a solution of 85.6 g. (1.10 moles) of methyl isothiocyanate, 93.9 area % pure, in 50 ml. of dry tetrahydrofuran, was added over 14 minutes at 4°–14° C with ice cooling. The cooling was removed and the mixture was stirred for an additional 2 hours. A strong argon purge was started and the excess sodium hydride was decomposed by the careful addition of 100 ml. of water. The tetrahydrofuran solvent was removed under reduced pressure and the residual product was drowned in 1500 ml. of water. The aqueous mixture was acidified with concentrated hydrochloric acid; solid which formed was extracted with 500 ml. of ethyl ether and the solution was washed with two 250 ml. portions of water, dried over anhydrous magnesium sulfate, filtered, concentrated and evaporated. There was obtained 203.7 g. (94.4% of theory) of O-2-chlorobenzyl methylthiocarbamate, m.p. 62.5°–65.5° C. The structure was confirmed by NMR and IR analyses.

The following Table I lists representative compounds of the present invention which can be prepared according to the above procedures.

Table I $$\underset{X}{\text{C}_6\text{H}_4}-\text{CH}_2-Y-\underset{\overset{|}{N}=R_1}{\overset{S-R}{C}}$$

| Compound No. | X | Y | R | $R_1$ | m.p. or $n_D^{30}$ |
|---|---|---|---|---|---|
| 1 | 2-Cl | O | $CH_3$ | $CH_3$ | 1.5630 |
| 2 | 2-Cl | O | $-CH_2CH=CH_2$ | $CH_3$ | 1.5601 |
| 3 | 2-Cl | O | n-$C_5H_{11}$ | $CH_3$ | 1.5370 |
| 4 | 2-Cl | O | $-CH_2-CCl=CH_2$ | $CH_3$ | 1.5698 |
| 5 | 2-F | O | $C_2H_5$ | $CH_3$ | 1.5263 |
| 6 | 2-Cl | O | $C_2H_5$ | $CH_3$ | 1.5526 |
| 7 | 2-Cl | O | n-$C_3H_7$ | $CH_3$ | 1.5456 |
| 8 | 2-Cl | O | i-$C_3H_7$ | $CH_3$ | 1.5464 |
| 9 | 2-Cl | O | n-$C_4H_9$ | $CH_3$ | 1.5380 |
| 10 | 2-Br | O | $CH_3$ | $CH_3$ | 1.5776 |
| 11 | 2-Br | O | $C_2H_5$ | $CH_3$ | 1.5679 |
| 12 | 2-Br | O | n-$C_3H_7$ | $CH_3$ | 1.5614 |
| 13 | 2-Br | O | i-$C_3H_7$ | $CH_3$ | 1.5621 |
| 14 | 2-Br | O | $-CH_2CH=CH_2$ | $CH_3$ | 1.5749 |
| 15 | 2-Br | O | n-$C_4H_9$ | $CH_3$ | 1.5542 |
| 16 | 2-Br | O | n-$C_5H_{11}$ | $CH_3$ | 1.5487 |
| 17 | 2-Br | O | $-CH_2-CCl=CH_2$ | $CH_3$ | 1.5827 |
| 18 | 2-F | O | $CH_3$ | $CH_3$ | 1.5321 |
| 19 | 2-Cl | O | $CH_3$ | $C_2H_5$ | 54–57.5° C |
| 20 | 2-F | O | n-$C_3H_7$ | $CH_3$ | 1.5219 |
| 21 | 2-F | O | $-CH_2CH=CH_2$ | $CH_3$ | 1.5342 |
| 22 | 2-F | O | i-$C_3H_7$ | $CH_3$ | 1.5200 |
| 23 | 2-F | O | n-$C_4H_9$ | $CH_3$ | 1.5161 |
| 24 | 2-F | O | n-$C_5H_{11}$ | $CH_3$ | 1.5120 |
| 25 | 2-F | O | n-$C_7H_{15}$ | $CH_3$ | 1.5069 |
| 26 | 2-F | O | $-CH_2CCl=CH_2$ | $CH_3$ | 1.5420 |
| 27 | 2-Br | O | n-$C_8H_{17}$ | $CH_3$ | 1.5321 |
| 28 | 2-I | O | $CH_3$ | $CH_3$ | 1.5099 |
| 29 | 2-I | O | $C_2H_5$ | $CH_3$ | 1.5949 |
| 30 | 2-Cl | O | $C_2H_5$ | $C_2H_5$ | 1.5422 |
| 31 | 2-Cl | O | n-$C_3H_7$ | $C_2H_5$ | 1.5297 |
| 32 | 2-Cl | O | i-$C_3H_7$ | $C_2H_5$ | 1.5348 |
| 33 | 2-Cl | O | n-$C_4H_9$ | $C_2H_5$ | 1.5316 |
| 34 | 2-Cl | O | $-CH_2CH=CH_2$ | $C_2H_5$ | 1.5483 |
| 35 | 2-Cl | O | $-CH_2-C(CH_3)=CH_2$ | $CH_3$ | 1.5520 |
| 36 | 2-Cl | O | $-CH_2-C(CH_3)=CH_2$ | $C_2H_5$ | 1.6441 |
| 37 | 2-Cl | O | $-CH_2-CCl=CH_2$ | $C_2H_5$ | 1.5561 |
| 38 | 2-F | O | $-CH_2-C(CH_3)=CH_2$ | $CH_3$ | 1.5292 |
| 39 | 2-Br | O | $-CH_2-C(CH_3)=CH_2$ | $CH_3$ | 1.5666 |
| 40 | 2-I | O | n-$C_3H_7$ | $CH_3$ | 1.5860 |
| 41 | 2-I | O | i-$C_3H_7$ | $CH_3$ | 1.5846 |
| 42 | 2-I | O | $-CH_2CH=CH_2$ | $CH_3$ | 1.5992 |
| 43 | 2-I | O | $-CH_2-C(CH_3)=CH_2$ | $CH_3$ | 1.5914 |
| 44 | 2-I | O | n-$C_4H_9$ | $CH_3$ | 1.5773 |
| 45 | 2-I | O | n-$C_5H_{11}$ | $CH_3$ | 1.5708 |
| 46 | 2-Cl | O | $CH_3$ | n-$C_4H_9$ | 1.5347 |
| 47 | 2-Cl | O | $C_2H_5$ | n-$C_4H_9$ | 1.5296 |
| 48 | 2-Cl | O | n-$C_3H_7$ | n-$C_4H_9$ | 1.5248 |
| 49 | 2-Cl | O | i-$C_3H_7$ | n-$C_4H_9$ | 1.5234 |
| 50 | 2-Cl | O | $CH_2CH=CH_2$ | n-$C_4H_9$ | 1.5357 |
| 51 | 2-Cl | O | n-$C_4H_9$ | n-$C_4H_9$ | 1.5211 |
| 52 | 2-Cl | O | n-$C_6H_{13}$ | $CH_3$ | 1.5292 |
| 53 | 2-Cl | O | n-$C_7H_{15}$ | $CH_3$ | 1.5252 |
| 54 | 2-Cl | O | n-$C_8H_{17}$ | $CH_3$ | 1.5211 |
| 55 | 2-Cl | O | n-$C_{10}H_{21}$ | $CH_3$ | 1.5146 |
| 56 | 2-Cl | O | n-$C_{12}H_{25}$ | $CH_3$ | 1.5105 |
| 57 | 2-Cl | O | $C_2H_5$ | n-$C_3H_7$ | 1.5341 |
| 58 | 2-Cl | O | n-$C_3H_7$ | n-$C_3H_7$ | 1.5310 |
| 59 | 3-Cl | O | $CH_3$ | $CH_3$ | 1.5569 |
| 60 | 2-Cl | O | $CH_3$ | n-$C_3H_7$ | 1.5424 |
| 61 | 2-Cl | O | $-CH_2CH=CH_2$ | n-$C_3H_7$ | 1.5429 |
| 62 | 3-Cl | O | $C_2H_5$ | $CH_3$ | 1.5516 |
| 63 | 3-Cl | O | n-$C_3H_7$ | $CH_3$ | 1.5449 |
| 64 | 3-Cl | O | i-$C_3H_7$ | $CH_3$ | 1.5432 |
| 65 | 3-Cl | O | $-CH_2CH=CH_2$ | $CH_3$ | 1.5589 |
| 66 | 3-Cl | O | n-$C_4H_9$ | $CH_3$ | 1.5395 |
| 67 | 3-Cl | O | $C_2H_5$ | $C_2H_5$ | 1.5401 |
| 68 | 2,6-Cl | O | $C_2H_5$ | $CH_3$ | 1.5654 |
| 69 | 2-Cl | O | $-CH_2SCH_3$ | $CH_3$ | 1.5825 |
| 70 | 3-Cl | O | $CH_3$ | $C_2H_5$ | 1.5480 |
| 71 | 2,6-Cl | O | n-$C_3H_7$ | $CH_3$ | 1.5564 |
| 72 | 3-Cl | O | n-$C_3H_7$ | $C_2H_5$ | 1.5340 |
| 73 | 3-Cl | O | $-CH_2-C(CH_3)=CH_2$ | $C_2H_5$ | 1.5425 |
| 74 | 2,6-Cl | O | $-CH_2-C(CH_3)=CH_2$ | $CH_3$ | 1.5643 |
| 75 | 2,4-Cl | O | $C_2H_5$ | $CH_3$ | 1.5633 |
| 76 | 2,4-Cl | O | n-$C_3H_7$ | $CH_3$ | 1.5549 |
| 77 | 2,4-Cl | O | $CH_2-C(CH_3)=CH_2$ | $CH_3$ | 1.5634 |

Table I-continued $$\underset{X}{\underset{|}{\text{C}_6\text{H}_4}}-\text{CH}_2-Y-\underset{\underset{N-R_1}{\parallel}}{\overset{S-R}{\underset{|}{C}}}$$

| Compound No. | X | Y | R | $R_1$ | m.p. or $n_D^{30}$ |
|---|---|---|---|---|---|
| 78 | 2-Cl | O | —CH$_2$CH=CHCH$_3$ | CH$_3$ | 1.5550 |
| 79 | 3,4-Cl | O | n-C$_3$H$_7$ | CH$_3$ | 1.5555 |
| 80 | 3,4-Cl | O | —CH$_2$CH=CH$_2$ | CH$_3$ | 1.5703 |
| 81 | 3,4-Cl | O | —CH$_2$C(CH$_3$)=CH$_2$ | CH$_3$ | 1.5631 |
| 82 | 2-Cl | O | —CH$_2$—C(=O)—OCH$_3$ | CH$_3$ | 1.5488 |
| 83 | 2,5-Cl | O | n-C$_3$H$_7$ | CH$_3$ | 1.5569 |
| 84 | 2,5-Cl | O | —CH$_2$CH=CH$_2$ | CH$_3$ | 46–49.5° C |
| 85 | 2,5-Cl | O | —CH$_2$—C(CH$_3$)=CH$_2$ | CH$_3$ | * |
| 86 | H | O | n-C$_3$H$_7$ | CH$_3$ | 1.5357 |
| 87 | H | O | —CH$_2$CH=CH$_2$ | CH$_3$ | 1.5516 |
| 88 | H | O | —CH$_2$—C(CH$_3$)=CH$_2$ | CH$_3$ | 1.5462 |
| 89 | 2-Cl | O | n-C$_3$H$_7$ | i-C$_3$H$_7$ | 1.5288 |
| 90 | 2-Cl | O | —CH$_2$CH=CH$_2$ | i-C$_3$H$_7$ | 1.5404 |
| 91 | 2-Cl | O | —CH$_2$—C(CH$_3$)=CH$_2$ | i-C$_3$H$_7$ | 1.5364 |
| 92 | 2-Cl | O | n-C$_3$H$_7$ | t-C$_4$H$_9$ | 1.5235 |
| 93 | 2-Cl | O | —CH$_2$CH=CH$_2$ | t-C$_4$H$_9$ | 1.5346 |
| 94 | 2-Cl | O | n-C$_4$H$_9$ | t-C$_4$H$_9$ | 1.5190 |
| 95 | 2-Cl | O | —CH$_2$C(CH$_3$)=CH$_2$ | t-C$_4$H$_9$ | 1.5323 |
| 96 | 2-CH$_3$ | O | n-C$_3$H$_7$ | CH$_3$ | 1.5362 |
| 97 | 2-CH$_3$ | O | —CH$_2$CH=CH$_2$ | CH$_3$ | 1.5503 |
| 98 | 2-CH$_3$ | O | —CH$_2$—C(CH$_3$)=CH$_2$ | CH$_3$ | 1.5448 |
| 99 | 2-F | O | —CH$_2$CH$_2$Cl | CH$_3$ | 1.5406 |
| 100 | 2-Cl | O | n-C$_3$H$_7$ | —CH$_2$—C$_6$H$_4$—Cl | 1.5783 |
| 101 | 2-Cl | O | —CH$_2$CH$_2$CH$_2$Cl | CH$_3$ | 1.5601 |
| 102 | 2-Cl | O | n-C$_3$H$_7$ | —CH$_2$CH=CH$_2$ | 1.5461 |
| 103 | 2-Cl | O | —CH$_2$CH=CH$_2$ | —CH$_2$CH=CH$_2$ | 1.5587 |
| 104 | 2-Cl | O | —CH$_2$—C(CH$_3$)=CH$_2$ | —CH$_2$CH=CH$_2$ | 1.5507 |
| 105 | 2-Cl | O | C$_2$H$_5$ | —CH$_2$—C$_6$H$_4$—Cl | 1.5881 |
| 106 | 4-Cl | O | CH$_3$ | C$_2$H$_5$ | 1.5486 |
| 107 | 4-Cl | O | C$_2$H$_5$ | C$_2$H$_5$ | 1.5415 |
| 108 | 4-Cl | O | n-C$_3$H$_7$ | C$_2$H$_5$ | 1.5366 |
| 109 | 4-Cl | O | n-C$_4$H$_9$ | C$_2$H$_5$ | 1.5322 |
| 110 | 4-Cl | O | n-C$_5$H$_{11}$ | C$_2$H$_5$ | 1.5282 |
| 111 | 4-Cl | O | n-C$_6$H$_{13}$ | C$_2$H$_5$ | 1.5254 |
| 112 | 4-Cl | O | n-C$_7$H$_{15}$ | C$_2$H$_5$ | 1.5217 |
| 113 | 2-Cl | S | CH$_3$ | CH$_3$ | 1.6062 |
| 114 | 2-Cl | S | C$_2$H$_5$ | CH$_3$ | 1.5948 |
| 115 | 2-Cl | S | n-C$_3$H$_7$ | CH$_3$ | 1.5879 |
| 116 | 2-Cl | S | —CH$_2$CH=CH$_2$ | CH$_3$ | 1.6005 |
| 117 | 2-Cl | O | —CH$_2$CH=CH$_2$ | —CH$_2$—C$_6$H$_4$—Cl | 1.5892 |
| 118 | 2-Cl | O | —CH$_2$—C(CH$_3$)=CH$_2$ | —CH$_2$—C$_6$H$_4$—Cl | 1.5823 |
| 119 | H | O | C$_2$H$_5$ | CH$_3$ | 1.5433 |
| 120 | H | O | n-C$_4$H$_9$ | CH$_3$ | 1.5291 |
| 121 | H | O | n-C$_5$H$_{11}$ | CH$_3$ | 1.5261 |
| 122 | H | O | C$_2$H$_5$ | C$_2$H$_5$ | 1.5280 |
| 123 | H | O | n-C$_3$H$_7$ | C$_2$H$_5$ | 1.5254 |
| 124 | H | O | n-C$_4$H$_9$ | C$_2$H$_5$ | 1.5211 |
| 125 | H | O | n-C$_5$H$_{11}$ | C$_2$H$_5$ | 1.5172 |

*Soapy solid

Aphicidal Evaluation Tests

Tests were conducted on two species of aphids, namely the black bean aphid, *Aphis fabae* (Scop.) and the green peach aphid, *Myzus persicae* (Sulzer) as follows:

*Black Bean Aphid*: Nasturtium plants (*Tropaeolum sp.*), approximately 5 cm tall, were transplanted into sandy loam soil in 3-inch clay pots and infested with 25–50 black bean aphids of mixed ages. 24 hours later, they were sprayed to the point of runoff with 50—50 acetone-water solutions of the test chemicals. Treated plants were held in the greenhouse and mortality was recorded after 7 days. Test concentrations ranged from 0.05% down to that at which 50% mortality occurred. LD-50 values are expressed below in Table II under the heading "BA" in terms of percent of the test compound in the sprayed solution.

*Green Peach Aphid*: Radish plants (*Rhaphanus sativus*), approximately 2 cm tall, were transplanted into sandy loam soil in 3-inch clay pots and infested with 25–50 green peach aphids of mixed ages. 24 hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "GPA" in terms of percent of the test compound in the sprayed solution.

Table II

| Compound No. | BA (%) | GPA (%) |
|---|---|---|
| 1 | 0.05 | — |
| 2 | 0.008 | 0.005 |
| 3 | 0.03 | — |
| 4 | 0.01 | 0.03 |
| 5 | 0.003 | 0.003 |
| 6 | 0.0008 | 0.003 |
| 7 | 0.0003 | 0.003 |
| 8 | 0.0008 | 0.003 |
| 9 | 0.0005 | 0.003 |
| 10 | 0.003 | 0.003 |
| 11 | 0.003 | 0.003 |
| 12 | 0.0008 | 0.003 |
| 13 | 0.0008 | 0.003 |
| 14 | 0.0008 | 0.003 |
| 15 | 0.003 | 0.003 |
| 16 | 0.003 | 0.003 |
| 17 | 0.05 | — |
| 18 | 0.005 | 0.03 |
| 19 | 0.005 | 0.008 |
| 20 | 0.0005 | 0.003 |
| 21 | 0.0003 | 0.003 |
| 22 | 0.003 | 0.003 |
| 23 | 0.003 | 0.003 |
| 24 | 0.003 | 0.005 |
| 25 | 0.003 | 0.003 |
| 26 | 0.003 | 0.003 |
| 27 | 0.008 | 0.05 |
| 28 | 0.01 | 0.03 |
| 29 | 0.005 | 0.003 |
| 30 | 0.003 | 0.005 |
| 31 | 0.0003 | 0.002 |
| 32 | 0.0005 | 0.002 |
| 33 | 0.0005 | 0.003 |
| 34 | 0.003 | 0.003 |
| 35 | 0.0005 | 0.0005 |
| 36 | 0.003 | 0.002 |
| 37 | 0.003 | 0.01 |
| 38 | 0.0003 | 0.002 |
| 39 | 0.002 | 0.002 |
| 40 | 0.005 | 0.003 |
| 41 | 0.005 | 0.005 |
| 42 | 0.005 | 0.03 |
| 43 | 0.002 | 0.005 |
| 44 | 0.003 | 0.03 |
| 45 | 0.05 | — |
| 46 | 0.003 | 0.03 |
| 47 | 0.01 | 0.03 |
| 48 | 0.002 | 0.01 |
| 49 | 0.03 | 0.03 |
| 50 | 0.0005 | 0.005 |
| 51 | 0.001 | 0.002 |
| 52 | 0.002 | 0.005 |
| 53 | 0.002 | 0.01 |
| 54 | 0.003 | 0.03 |
| 55 | 0.003 | 0.03 |
| 56 | 0.005 | >0.05 |
| 57 | 0.001 | 0.005 |
| 58 | 0.0005 | 0.01 |
| 59 | 0.005 | 0.03 |
| 60 | 0.005 | 0.03 |
| 61 | 0.002 | 0.01 |
| 62 | 0.005 | 0.03 |
| 63 | 0.003 | 0.005 |
| 64 | 0.005 | 0.01 |
| 65 | 0.003 | 0.03 |
| 66 | 0.005 | 0.03 |
| 67 | 0.05 | 0.05 |
| 68 | 0.05 | 0.05 |
| 69 | 0.002 | 0.003 |
| 70 | 0.01 | 0.03 |
| 71 | 0.04 | 0.03 |
| 72 | 0.01 | 0.05 |
| 73 | 0.005 | 0.03 |
| 74 | 0.05 | 0.01 |
| 75 | 0.03 | 0.03 |
| 76 | 0.03 | 0.03 |
| 77 | 0.05 | — |
| 78 | 0.001 | 0.005 |
| 79 | 0.005 | 0.05 |
| 80 | 0.01 | 0.05 |
| 81 | 0.005 | 0.03 |
| 82 | 0.003 | 0.03 |
| 83 | 0.03 | >0.05 |
| 84 | 0.05 | >0.05 |
| 85 | 0.03 | >0.05 |
| 86 | 0.001 | 0.005 |
| 87 | 0.002 | 0.01 |
| 88 | 0.002 | 0.003 |
| 89 | 0.005 | 0.03 |
| 90 | 0.005 | 0.03 |
| 91 | 0.008 | 0.03 |
| 92 | 0.03 | 0.03 |
| 93 | 0.005 | 0.03 |
| 94 | 0.03 | 0.03 |
| 95 | 0.008 | 0.03 |
| 96 | 0.002 | 0.002 |
| 97 | 0.002 | 0.003 |
| 98 | 0.003 | 0.002 |
| 99 | 0.05 | 0.03 |
| 100 | 0.05 | — |
| 101 | 0.002 | 0.003 |
| 102 | 0.0005 | 0.005 |
| 103 | 0.002 | 0.01 |
| 104 | 0.002 | 0.005 |
| 105 | 0.002 | 0.005 |
| 106 | 0.03 | 0.03 |
| 107 | 0.03 | 0.03 |
| 108 | 0.01 | 0.03 |
| 109 | 0.03 | 0.01 |
| 110 | 0.03 | 0.03 |
| 111 | 0.05 | 0.03 |
| 112 | >0.05 | 0.03 |
| 113 | 0.03 | 0.03 |
| 114 | 0.05 | — |
| 115 | 0.005 | 0.03 |
| 116 | 0.01 | 0.03 |
| 117 | 0.03 | >0.05 |
| 118 | 0.03 | >0.05 |
| 119 | 0.003 | 0.005 |
| 120 | 0.002 | 0.002 |
| 121 | 0.01 | 0.005 |
| 122 | 0.008 | 0.005 |
| 123 | 0.001 | 0.01 |
| 124 | 0.003 | 0.008 |
| 125 | 0.005 | 0.005 |

The compounds of this invention are generally embodied into a form suitable for convenient application. For example, the compounds can be embodied into aphicidal compositions which are provided in the form of emulsions, suspensions, solutions, dusts and aerosol sprays. In general, such compositions will contain, in addition to the active compounds, the adjuvants which are found normally in aphicidal preparations. In these compositions, the active compounds of this invention can be employed as the sole pesticidal component or they can be used in admixture with other compounds having similar utility. The pesticidal compositions of this invention can contain, as adjuvants, appropriate inert carriers or diluents, for example, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed aphicidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the aphicidal compositions containing compounds of this invention are used in any particular instance will be readily apparent to a person skilled in the art. Generally, the active compound will be embodied in the form of a liquid composition; for example, an emulsion, suspension, or aerosol spray. While the concentration of the active aphicide in the present compositions can vary within rather wide limits, ordinarily the aphicidal compound will comprise

What is claimed is:

1. A process for production of a compound having the formula

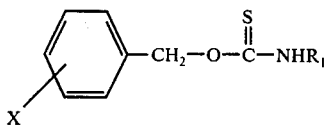

in which X is hydrogen, mono- or dihalo or 2-methyl and R₁ is lower alkyl, lower alkenyl or p-chlorobenzyl, comprising:

(a) reacting an alcohol having the formula

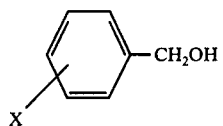

with sodium hydride in the presence of tetrahydrofuran; and (b) reacting the product of step (a) with a compound having the formula R₁-SCN.

2. A process according to claim 1 further comprising recovering the desired compound from the product of step (b).

* * * * *